(12) United States Patent
Soltesz et al.

(10) Patent No.: US 9,486,266 B2
(45) Date of Patent: *Nov. 8, 2016

(54) SELECTIVE LUNG TISSUE ABLATION

(71) Applicant: Pulmonx Corporation, Redwood City, CA (US)

(72) Inventors: Peter P. Soltesz, Henderson, NV (US); Nikolai Aljuri, Hillsborough, CA (US); Ajit Nair, Pleasanton, CA (US)

(73) Assignee: PulmonX Corporation, Redwood City, CA (US)

( * ) Notice: Subject to any disclaimer, the term of this patent is extended or adjusted under 35 U.S.C. 154(b) by 257 days.

This patent is subject to a terminal disclaimer.

(21) Appl. No.: 14/033,163

(22) Filed: Sep. 20, 2013

(65) Prior Publication Data

US 2014/0018605 A1 Jan. 16, 2014

Related U.S. Application Data

(63) Continuation of application No. 12/606,007, filed on Oct. 26, 2009, now Pat. No. 8,568,403, which is a continuation of application No. 11/460,860, filed on Jul. 28, 2006, now Pat. No. 7,628,789.

(60) Provisional application No. 60/709,376, filed on Aug. 17, 2005.

(51) Int. Cl.
| | | |
|---|---|---|
| A61B 18/14 | (2006.01) |
| A61B 18/02 | (2006.01) |
| A61B 18/08 | (2006.01) |
| A61B 18/12 | (2006.01) |
| A61B 18/18 | (2006.01) |
| A61M 16/00 | (2006.01) |
| A61M 16/04 | (2006.01) |
| A61N 5/10 | (2006.01) |

(Continued)

(52) U.S. Cl.
CPC ......... *A61B 18/0206* (2013.01); *A61B 18/082* (2013.01); *A61B 18/1206* (2013.01); *A61B 18/14* (2013.01); *A61B 18/1492* (2013.01); *A61B 18/1815* (2013.01); *A61M 16/0057* (2013.01); *A61M 16/0434* (2013.01); *A61M 16/0463* (2013.01); *A61N 5/1001* (2013.01); *A61N 7/022* (2013.01); *A61B 2018/00214* (2013.01); *A61B 2018/00541* (2013.01); *A61B 2018/044* (2013.01); *A61B 2018/1435* (2013.01)

(58) Field of Classification Search
CPC ................ A61B 18/1492; A61B 2018/00541; A61B 2018/1435; A61B 2018/1437; A61B 2018/00214; A61B 2018/1405
See application file for complete search history.

(56) References Cited

U.S. PATENT DOCUMENTS 5,061,274 A 10/1991 Kensey
5,972,026 A * 10/1999 Laufer .................. A61B 18/00
606/41

(Continued)

OTHER PUBLICATIONS

International search report and written opinion dated Jul. 3, 2008 for PCT/US2006/032418.

(Continued)

*Primary Examiner* — Michael Peffley
(74) *Attorney, Agent, or Firm* — Wilson Sonsini Goodrich & Rosati

(57) ABSTRACT

Medical methods and systems are provided for effecting lung volume reduction by selectively ablating segments of lung tissue.

20 Claims, 6 Drawing Sheets

(51) Int. Cl.
*A61N 7/02* (2006.01)
*A61B 18/00* (2006.01)
*A61B 18/04* (2006.01)

(56) References Cited

U.S. PATENT DOCUMENTS

| | | |
|---|---|---|
| 6,287,290 B1 | 9/2001 | Perkins et al. |
| 6,322,559 B1 * | 11/2001 | Daulton ............ A61B 18/1492 606/41 |
| 6,411,852 B1 | 6/2002 | Danek et al. |
| 6,488,673 B1 * | 12/2002 | Laufer ................ A61B 18/00 604/516 |
| 6,539,265 B2 | 3/2003 | Medhkour et al. |
| 6,645,205 B2 | 11/2003 | Ginn |
| 6,692,494 B1 | 2/2004 | Cooper et al. |
| 6,712,812 B2 * | 3/2004 | Roschak ............... A61B 8/445 606/41 |
| 7,291,146 B2 * | 11/2007 | Steinke ............. A61B 18/1492 606/41 |
| 7,628,789 B2 | 12/2009 | Soltesz et al. |
| 8,568,403 B2 | 10/2013 | Soltesz et al. |
| 2002/0049370 A1 | 4/2002 | Laufer et al. |
| 2002/0198523 A1 | 12/2002 | Behl |
| 2003/0051733 A1 | 3/2003 | Kotmel et al. |
| 2004/0102804 A1 | 5/2004 | Chin |
| 2006/0264772 A1 | 11/2006 | Aljuri et al. |

OTHER PUBLICATIONS

Office action dated Mar. 4, 2013 for U.S. Appl. No. 12/606,007.
Office action dated Nov. 13, 2008 for U.S. Appl. No. 11/460,860.

* cited by examiner

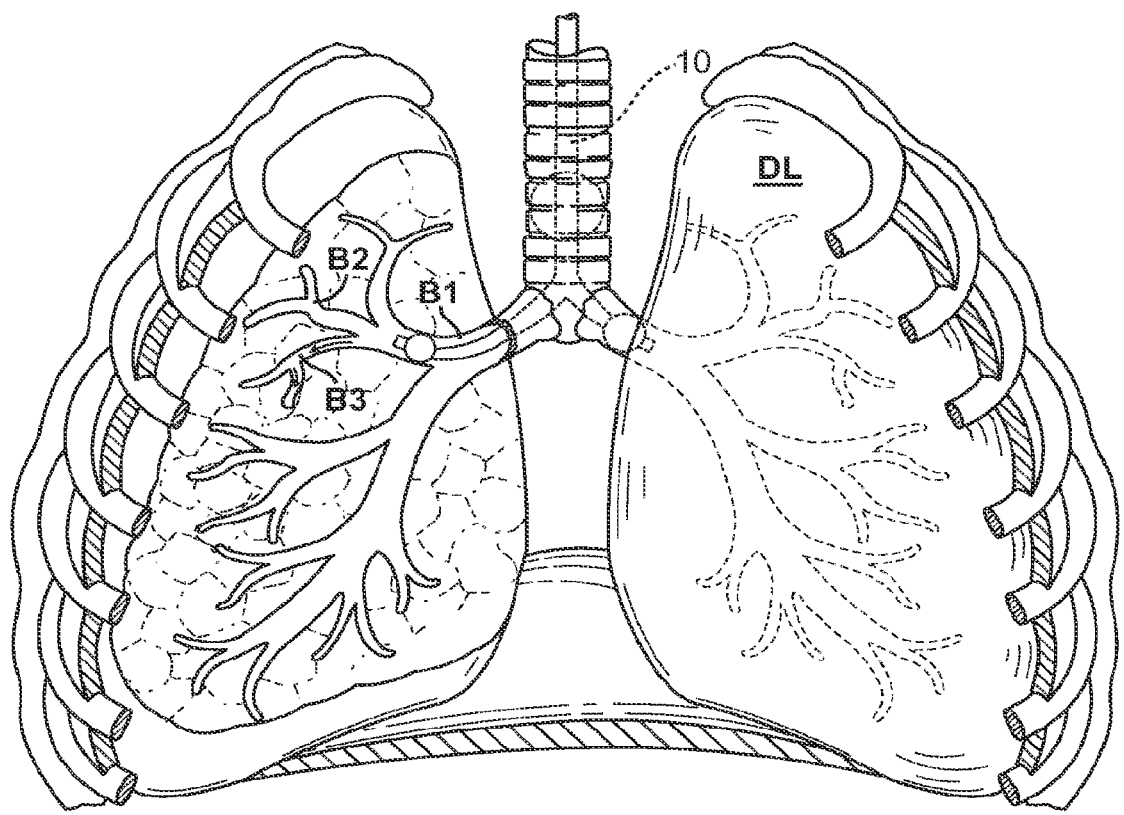
FIG. 1
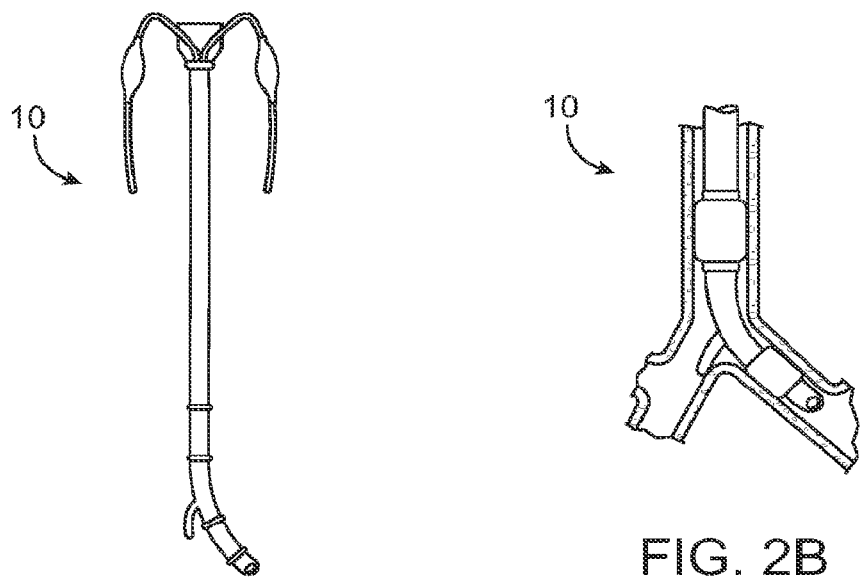
FIG. 2A
FIG. 2B

SELECTIVE LUNG TISSUE ABLATION

CROSS-REFERENCE TO RELATED APPLICATIONS

The present application is a continuation of U.S. application Ser. No. 12/606,007, now U.S. Pat. No. 8,568,403, filed Oct. 26, 2009, which is a continuation of U.S. application Ser. No. 11/460,860, now U.S. Pat. No. 7,628,789, filed Jul. 28, 2006, which claims the benefit of Provisional Application No. 60/709,376, filed Aug. 17, 2005, the full disclosures of which are incorporated herein by reference.

BACKGROUND OF THE INVENTION

Field of the Invention

The present invention relates generally to medical methods and apparatus. More particularly, the present invention relates to methods for selectively ablating target sites in the lung while protecting adjacent lung and tissue structures.

Chronic obstructive pulmonary disease is a significant medical problem affecting 16 million people or about 6% of the U.S. population. Specific diseases in this group include chronic bronchitis and emphysema. Emphysema is a condition of the lung characterized by the abnormal permanent enlargement of the airspaces distal to the terminal bronchiole, accompanied by the destruction of their walls, and without obvious fibrosis. It is known that emphysema and other pulmonary diseases reduce the ability of one or both lungs to fully expel air during the exhalation phase of the breathing cycle. One of the effects of such diseases is that the diseased lung tissue is less elastic than healthy lung tissue, which is one factor that prevents full exhalation of air. During breathing, the diseased portion of the lung does not fully recoil due to the emphysematic lung tissue being less elastic than healthy tissue. Consequently, the diseased lung tissue exerts a relatively low driving force, which results in the diseased lung expelling less air volume than a healthy lung. The reduced air volume exerts less force on the airway, which allows the airway to close before all air has been expelled (air trapping), another factor that prevents full exhalation. While a number of therapeutic interventions are used and have been proposed, none are completely effective, and chronic obstructive pulmonary disease remains the fourth most common cause of death in the United States. Thus, improved and alternative treatments and therapies would be of significant benefit.

Of particular interest to the present invention, lung function in patients suffering from emphysema and other chronic obstructive pulmonary diseases can be improved by reducing the effective lung volume, typically by resecting or otherwise isolating diseased portions of the lung. Resection of diseased portions of the lungs both promotes expansion of the non-diseased regions of the lung and decreases the portion of inhaled air which goes into the lungs but is unable to transfer oxygen to the blood. Lung reduction is conventionally performed in open chest or thoracoscopic procedures where part of the lung is resected, typically using stapling devices having integral cutting blades.

While effective in many cases, conventional lung reduction surgery is significantly traumatic to the patient, even when thoracoscopic procedures are employed. Such procedures often result in the unintentional removal of healthy lung tissue, and frequently leave perforations or other discontinuities in the lung which result in air leakage from the remaining lung. Even technically successful procedures can cause respiratory failure, pneumonia, death, and many older or compromised patients are not even candidates for these procedures.

The use of devices that intrathoracically isolate a diseased region of the lung in order to reduce the volume of the diseased region, such as by collapsing the diseased lung region, has recently been proposed. For example, self-expanding plugs, one-way valves, and other occlusion devices may be implanted in airways feeding a targeted region of the lung to isolate the region of the diseased lung region. However, even with the implanted isolation devices properly deployed, air can flow into the isolated lung region via a collateral pathway. This can result in the diseased region of the lung still receiving air even though the isolation devices were implanted into the direct pathways to the lung. Collateral flow can be, for example, air flow that flows between segments of a lung (intralobar collateral ventilation), or it can be, for example, air flow that flows between lobes of a lung (interlobar collateral ventilation). Collateral resistance is reduced in emphysema, and may be substantially lower than airway resistance. Fissures are often incomplete, allowing collateral ventilation to traverse lobes. It is axiomatic that absorptive atelectasis could not develop in patients after the occlusive devices were placed if occluded regions received more ventilation than the rate of gas absorption. Collateral channels were the only pathways available for such ventilation.

For these reasons, it would be desirable to provide improved methods, apparatus, and systems for treating diseased lung regions. In particular, it would be desirable to provide such methods, apparatus, and systems which are capable of treating diseased regions having collateral ventilation using principally or only intrabronchial access routes. It would be still further desirable if the present invention could provide for complete isolation of the diseased lung region while minimizing or eliminating any risk of injury or trauma to adjacent lung or other tissue structures. At least some of these objectives will be met by the inventions described hereinbelow.

BRIEF SUMMARY OF THE INVENTION

The present invention provides for improved and alternative methods, apparatus, and systems for the minimally-invasive treatment of diseased lung regions, such as those which arise from emphysema, bronchitis, or other diseases. The treatments may be performed endobronchially, typically through a transesophageal access route, and provide for substantially complete isolation of a target lung region, referred to hereinafter as a "target site," even when the region or site is subject to collateral ventilation which would render prior occlusive treatment protocols ineffective. Typically, the patients will be screened to determine if the target site is subject to collateral ventilation prior to performing the method of the present invention.

The target sites within the lung are typically treated by delivering heat or other energy to raise the temperature of tissue within the target site to a level, typically from 40.degree. C. to 95.degree. C., and for a time sufficient to induce complete or substantially complete tissue necrosis followed by collapse of the treated site. The energy is preferably delivered by a catheter or other elongate probe which may be transesophageally and intrabronchially introduced to one or more target airways within the target site. Typically, the treatment catheters will have energy-applying structures, such as electrodes, heat exchangers, optical heating elements, or the like, which are sufficiently long and/or conformable to access and fill most or all of the target airway(s) within the target site being treated. Typically, the energy-applying elements will have a length in the range from 2 cm to 20 cm, preferably from 5 cm to 10 cm.

Optionally, heat-transfer liquids and/or gases may be introduced into the airways within the target site to enhance heat distribution from the heat-transfer elements. The heat-transfer liquids and/or gases may themselves be heated and under some circumstances could be the sole energy-delivering medium used in the methods of the present invention. Further optionally, the temperature can be monitored within the treatment site to assure that the temperature is maintained in the desired treatment ranges. For example, electronic temperature sensors can be located on the catheter or probe within the target site and feedback control systems can be used to control the rate of energy delivered to maintain the desired temperature.

In a further aspect of the present invention, steps will usually be taken to protect adjacent regions in the lung and external tissue structures while energy is delivered to the target site. Typically, the entire lung in which the target site is located will be collapsed in order to isolate the lung tissue from the surrounding thoracic tissue structures. Usually, while the target lung is collapsed, the other patient lung will be actively ventilated both to cool the lung and to provide oxygen to the patient. In addition to collapsing the treatment lung, cold heat-transfer liquids or gases may be introduced to the lung lobes, segments, or sub-segments adjacent to the target site which is being treated.

Often, before treating a patient with the heating methods of the present invention, the target site of the patient will be tested for collateral ventilation using any one of a variety of techniques, as described in co-pending applications referenced below. As a result of such screening, patients where the diseased target site is subject to collateral ventilation, and who are therefore less likely to be successfully treated by prior occlusive techniques, may be treated by more rigorous methods of the present invention.

In a first aspect of the present invention, methods for selectively ablating a treatment site in a lung comprise advancing a treatment apparatus through an airway toward the treatment site in the lung. Energy is then delivered through the treatment apparatus to heat tissue within the treatment site to a level which destroys the tissue while protecting adjacent regions in the lung and surrounding tissue from thermal damage. The temperature of the tissue within the treatment site is typically raised to a level in the range from 40.degree. C. to 95.degree. C., typically from 70.degree. C. to 95.degree. C. The energy may take a variety of forms, including electrical energy, heat energy, light energy, sound energy, radiation from microwaves or radioisotopes, and combinations thereof. In exemplary embodiments, the delivered energy will be thermal, typically generated by current flow through a resistive coil or delivery of a hot fluid into the lung or, more typically, into a heat exchanger in the treatment apparatus. In all cases, however, the energy delivery may be enhanced by introduction of an electrically conductive and/or heat-exchange liquid or gas into the treatment site, typically through a lumen or other access provided by the treatment apparatus, optionally between two or more isolation balloons.

Complete and generally uniform distribution of the heat throughout the volume of the lung treatment site may be achieved in a variety of ways. In addition to delivering an auxiliary heating exchange medium, the treatment apparatus may include multiple heat exchange elements or components. For example, the heat exchange apparatus may include multiple electrodes, coils, heat exchange elements so that they may be placed in more than one airway within the volume of the treatment site. The multiple heat exchange elements may be included on a single treatment apparatus or could each be delivered by separate heat-transfer apparatus, such as separate catheters, probes, or the like.

While the energy is being delivered to the treatment site for raising the tissue temperature therein, measures will be taken to protect adjacent regions within the lung and within the surrounding thoracic cavity. Usually, the lung which comprises the treatment site will be collapsed to provide for physical spacing between the lung tissue and the upper thoracic cavity. For example, the lung may be punctured from the inside, preferably from a location within the treatment site, to create a pneumothorax to separate the lung from the chest wall. The puncture can then be sealed, optionally as part of the ablation of the treatment site, although use of an occlusal stent or other sealing plug may also be needed. In addition, the adjacent regions which are not being treated that are within the lung which is being treated, will further be treated, typically by circulating a cooling liquid, gas, or other medium to keep the temperature below the level associated with necrosis or thermal damage.

In a second aspect of the present invention, treatment apparatus for ablating a treatment site in a lung of a patient comprises a shaft having a proximal end and a distal end. An energy-emitting element may be disposed near the distal end of the shaft, where the energy-emitting element is configured to extend through and conform to an airway within the treatment site of the lung. In the exemplary embodiments, the energy-emitting element will comprise an elongate member which will extend through the target site in the lung, typically having a length in the range set forth above. The energy-emitting element may be, for example, an elongate coil-shaped electrode, an elongate, braided wire electrode, or the like. In all cases, the energy-emitting element may further include an expansion element which permits the energy-emitting element to be expanded to conform to a shape of the airway of the treatment site. For example, the expansion element may comprise an inflatable balloon, or may comprise a constraint which can be released to allow expansion of a self-expanding energy-emitting element. Optionally, the treatment apparatus may further comprise catheters for delivering electrically conductive and/or thermally conductive liquids, gels, or other fluids into the treatment site. Often the treatment apparatus will further include one or more isolation balloons for conducting the fluids to desired regions within the treatment site.

BRIEF DESCRIPTION OF THE DRAWINGS

FIG. 1 illustrates an embodiment of a double lumen tube advanced into the dependent lung.

FIGS. 2A-2B illustrate example double lumen tubes.

DETAILED DESCRIPTION OF THE INVENTION

The methods, apparatus, and systems of the present invention are used for delivering energy to diseased target sites within a patient lung for ablation and consequent isolation of the diseased segment to treat diseased lung regions resulting from emphysema, bronchitis, and other primary diseases. The treatment methods of the present invention are more rigorous than and intended as alternatives to the intrabronchial occlusion methods described previously for isolating diseased regions within a patient's lung. The methods of the present invention will be referred to generally hereinbelow as selective lung tissue ablation (SLTA).

Prior to treatment with the SLTA methods of the present invention, patients will usually be tested with a collateral ventilation (CV) test along with a segmental diagnostic test, such as described in U.S. patent application Ser. No. 11/296,951; and U.S. patent application Ser. No. 10/241,733, both incorporated herein by reference for all purposes. Patients who test negative for the collateral ventilation test could probably benefit from the less traumatic endobronchial volume reduction treatment, which relies on placing occlusal stents in their target lung regions (U.S. Pat. No. 6,287,290). Patients who test positive for the CV measurements could be considered for the more invasive SLTA treatment procedure described herein. However, it should be appreciated that patients may receive the SLTA treatment based on a variety of reasons and will not necessarily undergo CV testing prior to receiving SLTA treatment.

The SLTA methods of the present invention may be used particularly for a treatment site in a lung that is supplied air through one or more collateral pathways. Such ablation may be desired to induce collapse in the lung region. In accordance with one aspect of the invention, there is disclosed a method of inducing one lung ventilation (OLV) in the emphysematous patient. This may be achieved with the use of a variety of devices. For example, FIG. 1 illustrates an embodiment of a double lumen tube 10 (such as manufactured by Mallinkcrodt Corp.) advanced into the dependent lung DL. Double lumen tube 10 in the formula Carlens tube are illustrated in FIGS. 2A-2B. FIG. 2B illustrates the Carlens tube of FIG. 2A inserted in a body lumen at a bifurcation, as it would be placed in the tracheal-bronchial tree.

Figure 3A:
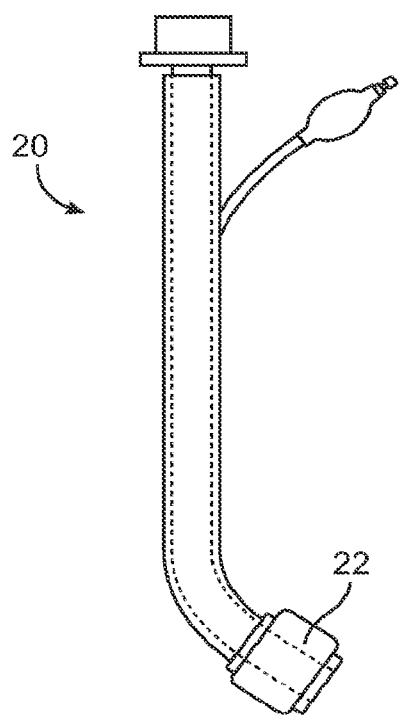
FIGS. 3A-3B illustrate example endobronchial tubes.
Figure 3B:
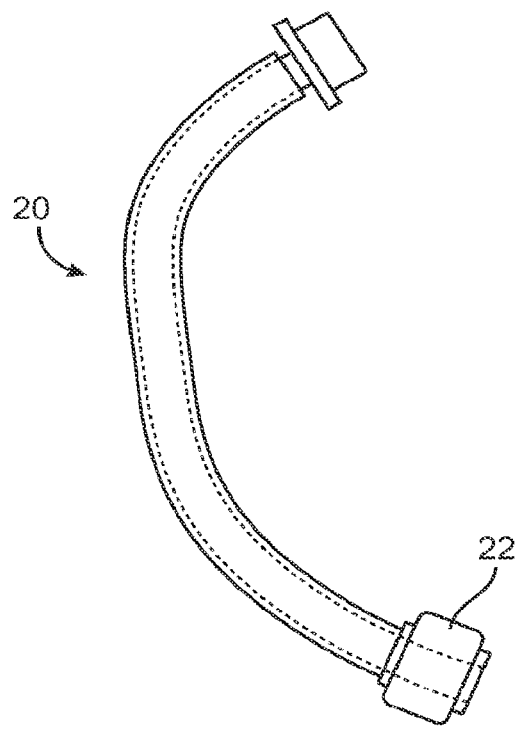
Figure 3C:
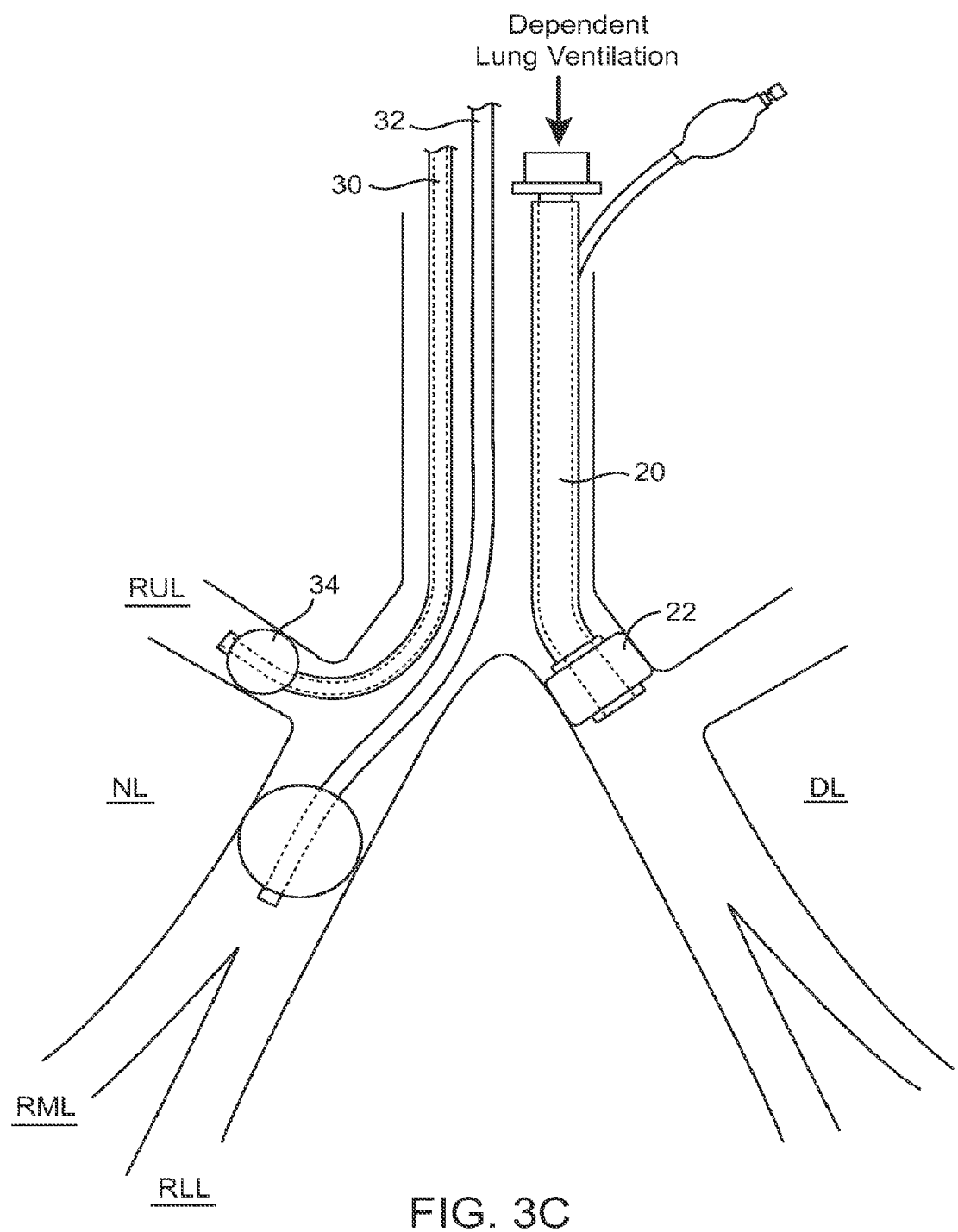
FIG. 3C illustrates the endobronchial tube of FIGS. 3A-3B positioned in the anatomy with a treatment apparatus.

OLV could also be introduced by other methods, such as with the use of an endobronchial blocker catheter. Or, with the use of a smaller diameter endobronchial tube 20, such as illustrated in FIGS. 3A-3B. The endobronchial tube may have, for example, a 6 mm ID and be shaped similarly to an endotracheal tube (C shaped to follow the curvature of the upper airway, but also would have a right or left sided curve for selective cannulation of the main stem bronchus). An isolation cuff 22 may have in general shape and pressure/volume characteristics which are similar to an endotracheal tube, however the cuff diameter would be smaller to accommodate the smaller size of the mainstem bronchus. This design would allow the bronchoscopist to advance any treatment apparatus alongside the tube while providing the necessary OLV procedure, as illustrated in FIG. 3C.

The left side of the lung (dependent lung DL) can thus be isolated and ventilated from the right side of the lung (nondependent lung NL). By puncturing the chest wall with a needle placed percutaneously, the nondependent lung NL can be collapsed. Alternatively, the puncture could be created from inside the inside of the lung, preferably through the wall adjacent to the treatment site that will be sealed during ablation. This separates the target lung region(s) from the chest wall which is intended to minimize thermal damage which may be caused by the ablation process.

Figure 4:
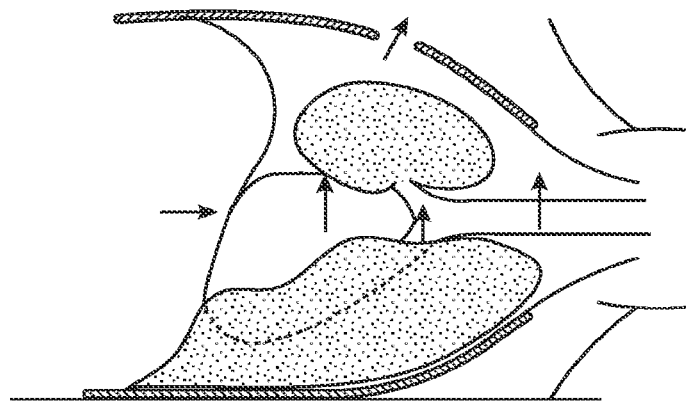
FIGS. 4-5 illustrate isolation/aspiration procedures.
Figure 5:
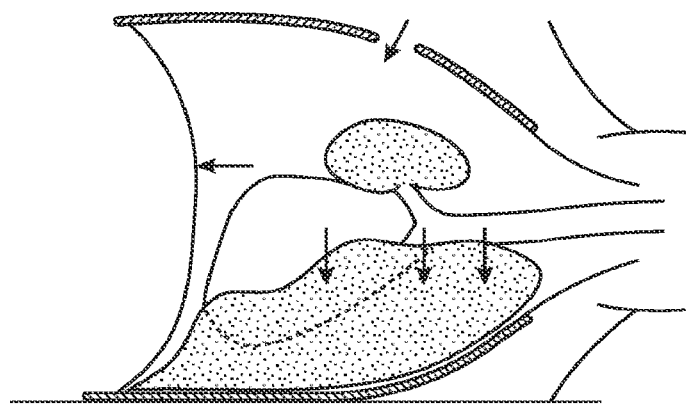

Since emphysematous or other diseased lung tissue may not collapse easily on it's own, an isolation/aspiration procedure may optionally be performed to collapse the target lung region as much as possible. If, for example, the right upper lobe is diseased, an isolation sheath 30 may be introduced over a bronchoscope (as described in U.S. Pat. No. 6,585,639 incorporated herein by reference for all purposes) to isolate the target site (lobe or segment). An additional balloon tipped isolation catheter 32 may be introduced alongside of the sheath/bronchoscope device. The balloon 34 would be positioned the way, that the feeding bronchus to the RML (right middle lobe) and RLL (right lower lobe) both would get occluded. This would close airflow to the RML and RLL, and would prevent collateral channels to backfill the target RUL, thus enhance the collapse of the target lung area. Both of these devices may be introduced, for example, either via a double lumen tube or alongside of an endobronchial tube. After inflating the balloons, an aspiration device may be connected to the working channel of the bronchoscope to facilitate the collapse of the target lung region. The target lung region is thus collapsed as much as possible, as illustrated in FIG. 4 (expiration) and FIG. 5 (inspiration). A treatment apparatus may then be positioned at the treatment site.

Figure 6A:
FIGS. 6A-6B, 7, and 8A-8B illustrate embodiments of treatment apparatuses.
Figure 6B:
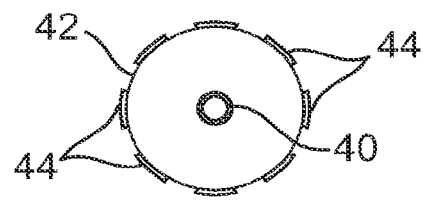
Figure 7:
Figure 8A:
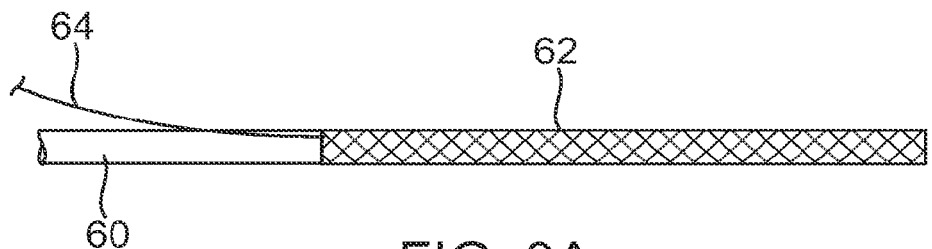
Figure 8B:
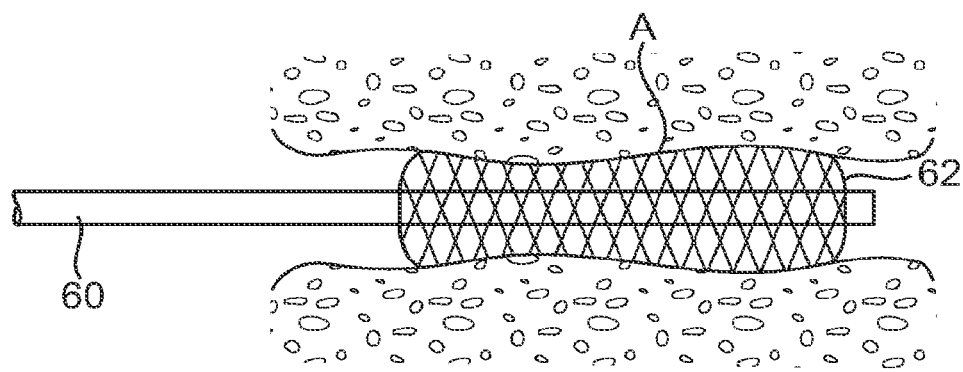

Exemplary treatment apparatuses include a balloon tipped catheter, illustrated in FIGS. 6A-6B, a coil tipped catheter, illustrated in FIG. 7, and a braided wire electrode catheter, illustrated in FIGS. 8A-8B. The balloon-tipped catheter 40 comprises an inflatable balloon 42 or other radially expandable structure having a plurality of electrodes 44 on its outer surface. Inflation of a balloon within an airway of the target site of the lung can thus engage the multiple electrodes against the wall of the airway in order to deliver radiofrequency or other energy, as discussed below. The catheter 50 includes a radially expandably coil-shaped electrode 52 which is flexible and able to conform to the shape and size of the airway in which it is deployed. The catheter 60 carries a self-expanding braided wire electrode structure 62 which is carried in its non-expanded configuration while the catheter 60 is delivered to its target site within the lung. The electrode structure may then be released from constraint, for example, using a release wire 64 which is threaded through the braided electrode. Alternatively, the braided wire electrode structure 62 may be covered with a sheath (not shown) or other restraining structure which may be pulled back to release the sheath so that it can self-expand. In either case, the braided electrode structure can assume an expanded configuration which conforms to the inner wall of the airway A, as shown in FIG. 8B. In all cases, it may be desirable to introduce a conductive gel through the treatment site to enhance electrical conduction. The gel could be introduced on or by the treatment catheters or by other catheters or probes.

The treatment apparatus is positioned at the treatment site (for example one placed in segment B1 and an other placed in B2 of FIG. 1), and a bipolar RF generator may be activated to provide suitable radiofrequency (RF) energy, preferably at a selected frequency in the range of 10 MHz to 1000 MHz. The emitted energy is converted within the tissue into heat in the range of about 40.degree. C. to about 95.degree. C. As the temperature increases, it is believed that the collagen undergoes a structural transformation whereby the collagen fibers contract and new cross links are formed. If a full lobar ablation is needed, two, three, or more electrode catheters could be placed and either monopolar or bipolar RF energy could be used.

Selective thermal ablation of the lung tissue is believed to cause the collagen matrix to shrink, thereby reducing the size of the target lung segment as well as closing up the collateral channels to prevent reinflation. Deleterious effects in the cells making up the tissue begin to occur at about 42.degree. C. As the temperature of the tissue increases because of the heat generated by the tissue's resistance, the tissue will undergo profound changes and eventually, as the temperature becomes high enough, that is, generally greater than 45.degree. C., the cells will die. The change of tissue resistance or impedance could be monitored and used for controlling the depth of ablation. The zone of cell death is known as a lesion and the procedure followed to create the lesion is commonly called an ablation. As the temperature increases beyond cell death temperature, complete disintegration of the cell walls and cells caused by boiling off of the tissue's water can occur. Cell death temperatures can vary somewhat with the type of tissue to which the power is being applied, but generally will begin to occur within the range of 45.degree. C. to 60.degree. C., though actual cell death of certain tissue cells may occur at a higher temperature. Optionally, polymerizing gels can be introduced to the treatment site to promote collagen cross-linking and lung volume reduction.

In addition to RF energy, other forms of energy including alternating electrical current, microwave, ultrasound, and optical, such as coherent (e.g., laser) or incoherent (e.g., light emitting diode or tungsten filament), can be used, as well as thermal energy generated from an electrically resistive coil, a hot fluid element (e.g., circulating liquids, gases, combinations of liquids and gases, etc.), radioisotopes, and the like. Thermal energy also includes the use of cold media (cryo ablation). The hot fluid element may comprise, for example, an elongated member that includes a conduit system whereby heated fluid is transported through the center of the member and then channeled outward toward the inner surface of the member. In one embodiment the heated fluid is diverted to contact the inner surface of the elongated member so that energy radiates from selected areas on the outer surface of the member corresponding to areas. Regardless of the source, energy delivered to the target lung tissue should be such that only the selected lung regions are ablated, while they are away from the chest wall to minimize thermal damage. Optionally, tissue contraction and volume reduction can be enhanced by immediately cooling a heat-ablated treatment site. For example, liquid nitrogen can be introduced following ablation to induce permanent cross-linking of the collagen.

Neighboring lobes or segments can be ventilated or just pressurized by a cooler gas or liquid to minimize thermal damage to them as well. The isolation catheter 32 of FIG. 3C may be used to deliver cooling media to neighboring lobes, segments, or subsegments of the lung being treated. The balloon 34 tipped isolation catheter 30 would be introduced alongside of the treatment catheter 30. The balloon would be positioned in a manner so that the feeding bronchus to the RML (right middle lobe) and RLL (right lower lobe) both would be occluded. Both of these catheters would be introduced either via the double lumen tube or alongside of the EB tube. Treatment can be done on only one segment or a plurality of segments at once. The cooling media can be any gas or liquid, for example cooled air, cooled oxygen, or a cooled liquid, such as saline or perfluorocarbon, etc. By controlling the pressure and temperature simultaneously between the target lung region versus the neighboring lung tissue, selective lung tissue ablation can be achieved with minimal thermal damage to the non-targeted sites.

A conductive liquid such as isotonic or hypertonic saline could also be introduced into a lobe or a segment. Air would be desirable to be removed prior to instilling the liquid. An electrode pad may be placed under the patient's chest to provide grounding. Once the liquid is in place, an electrode or plurality of electrodes would be inserted into the proximal end of the liquid pathway to communicate electrically with the instilled conductive liquid. A monopolar RF source could be activated to cause the liquid to heat up to a specific temperature.

Figure 9:
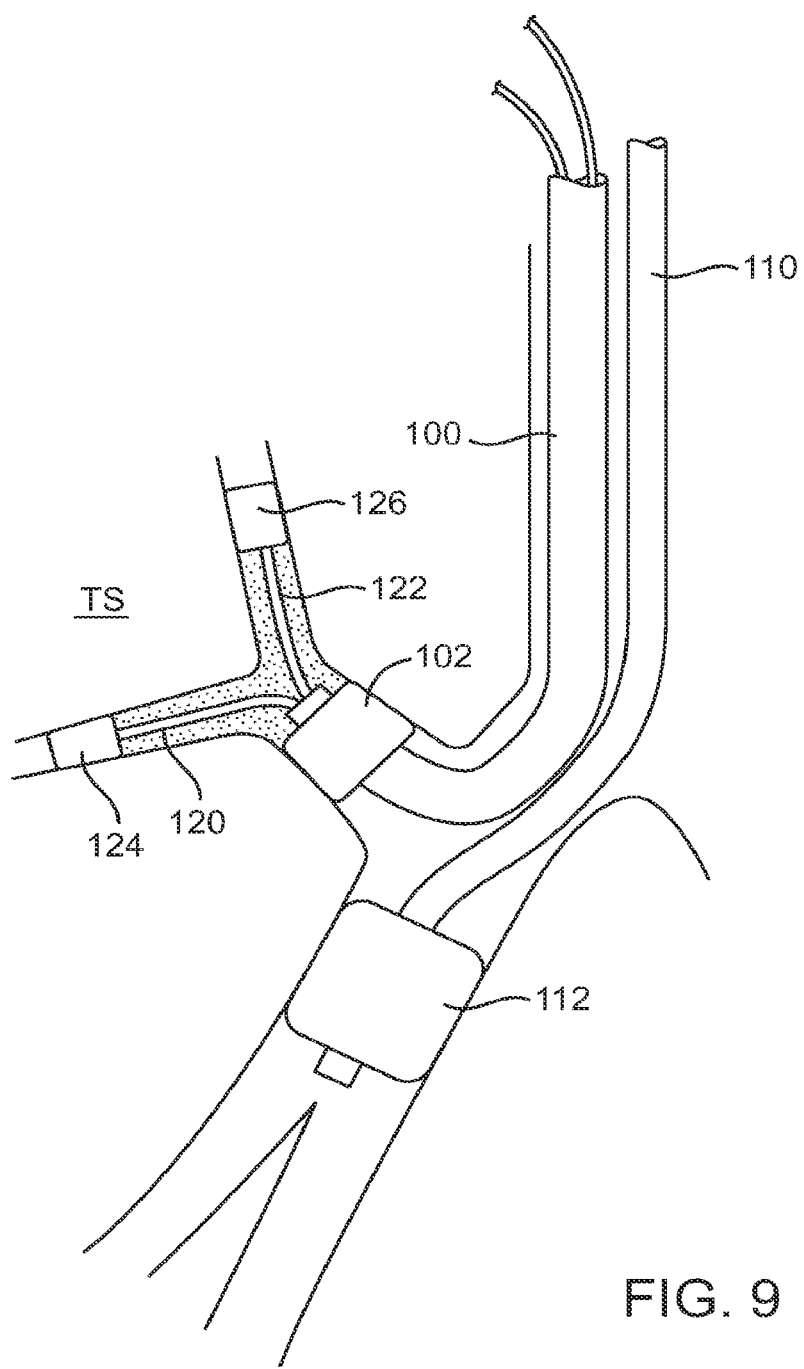
FIG. 9 illustrates the use of isolation balloons for containing an electrical or thermal conduction fluid within a treatment site.

Referring now to FIG. 9, a treatment site TS in the right upper lung is isolated with a balloon catheter 100 having an isolation balloon 102 at its distal end. The right lower lung is isolated with a second balloon catheter 110 having an isolation balloon 112 at its lower end. A pair of secondary balloon catheters 120, 122 having isolation balloons 124, 126 is introduced through a central lumen of the catheter 100. The isolation balloons 124, 126 are advanced into selected airways and inflated to create an isolated region between the balloon 102 and the more distal isolation balloons 124 and 126. It will be appreciated that in some instances only a single secondary isolation balloon would be used, while in other instances, three or more secondary isolation balloons could be used. In all cases, an electrically or thermally conductive fluid is introduced through the catheter 100 into the isolated region created between the isolation balloons 102, 124, and 126. Energy can be transferred with the treatment site TS by delivering energy into the fluid, or optionally cooling the fluid to remove energy from the treatment site. In the case of electrically conductive fluids, radiofrequency or other energy may be introduced into the fluid from catheter 100, where the energy will be conducted throughout the electrically conductive fluid to treat the tissue. Alternatively, electrodes could be provided on the catheters 120 and 122. Still further alternatively, heating elements could be placed on the catheters 120 and 122, or elsewhere within the system in order to heat thermally conductive fluids.

Other alternative treatment is possible for closing up collateral channels: same One Lung Ventilation (OLV) technique combined with Video Assisted Thoracoscopic Surgery (VATS) and mechanically by clipping or using an RF based cut and seal device to separate the incomplete fissures between lobes. After that either EVR could be performed by placing the occlusal stents or thermal ablation would be required.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A treatment system for ablating a targeted treatment site in a lung of a patient, comprising:
   a shaft having a proximal end and a distal end;
   an energy emitting element disposed near the distal end of the shaft, wherein the energy-emitting element is configured to extend through and conform to an airway in the targeted treatment site of the lung;
   one or more electronic temperature sensors; and
   one or more isolation catheters configured to deliver cooling media to neighboring lung tissue of the targeted treatment site of the lung;
   wherein said sensors are connected to a feedback control system configured to control the pressure and temperature simultaneously between the targeted treatment site versus the neighboring lung tissue to selectively ablate lung tissue.

2. A treatment apparatus as in claim 1, wherein the energy emitting element comprises an elongate coil shaped electrode.

3. A treatment apparatus as in claim 1, wherein the energy emitting element comprises an elongate braided wire electrode.

4. A treatment apparatus as in claim 1, wherein the energy-emitting element includes an expansion element which expands the energy emitting element to conform to a shape of the airway of the treatment site.

5. A treatment apparatus as in claim 4, wherein the expansion element comprises an inflatable balloon.

6. A treatment apparatus as in claim 4, wherein the expansion element comprises a constraint which can be released to allow the expansion element to self-expand.

7. A treatment apparatus as in claim 1, wherein the energy emitting element comprises au electrically resistive coil or a hot fluid element.

8. A method for selectively ablating a treatment region in a lung comprising:
   advancing a treatment apparatus through an airway toward the treatment region in the lung;
   exchanging energy through the treatment apparatus to heat or cool the treatment region to a level which destroys tissue at the region; and
   protecting adjacent regions in the lung and surrounding tissue from thermal damage by controlling pressure or temperature at the treatment region and at one or more untreated regions adjacent the treatment region.

9. A method as in claim 8, wherein the tissue is raised to a temperature in the range from 40° C. to 95° C.

10. A method as in claim 8, wherein the delivered energy comprises radiofrequency, alternating current, microwave, ultrasound, coherent light, incoherent light, radioisotopes, or a combination thereof.

11. A method as in claim 8, further comprising advancing at least one additional treatment apparatus toward the treatment site in the lung region and delivering energy to the treatment site through at least two treatment apparatuses.

12. A method as in claim 8, further comprising ventilating the patient's other lung.

13. A method as in claim 12, further comprising ventilating untreated region(s) of the lung adjacent to the treated region.

14. A method as in claim 8, further comprising collapsing the lung containing the lung under treatment prior to heating a treatment site.

15. A method as in claim 8, further comprising controlling pressure and temperature simultaneously in the treatment site and in the one or more untreated regions adjacent the treatment site so that thermal damage to the non-targeted sites is minimized.

16. A method as in claim 8, further comprising introducing an electrically or thermally conducting fluid into the treatment site to improve energy distribution.

17. A method as in claim 16, further comprising deploying isolation barriers to inhibit the conductive fluid from migrating from the treatment site.

18. A method as in claim 8, wherein the treatment site comprises an entire lobe of the lung.

19. A method as in claim 8, further comprising monitoring the temperature within the treatment site and controlling the energy exchange to maintain a temperature within a desired range.

20. A method as in claim 8, further comprising:
   testing the patient to determine if the treatment site is subject to collateral ventilation; and
   ablating the treatment site only if the treatment site is subject to collateral ventilation.

* * * * *